(12) United States Patent
Hori et al.

(10) Patent No.: US 6,191,809 B1
(45) Date of Patent: Feb. 20, 2001

(54) METHOD AND APPARATUS FOR ALIGNING STEREO IMAGES

(75) Inventors: Koichiro Hori; Herbert A. Thaler, both of Framingham, MA (US)

(73) Assignee: Vista Medical Technologies, Inc., Carlsbad, CA (US)

( * ) Notice: Under 35 U.S.C. 154(b), the term of this patent shall be extended for 0 days.

(21) Appl. No.: 09/007,469

(22) Filed: Jan. 15, 1998

(51) Int. Cl.[7] .................. H04N 13/00; H04N 15/00
(52) U.S. Cl. .................. 348/45; 348/48; 348/51; 600/109
(58) Field of Search ................ 348/42, 45, 46, 348/47, 48, 65, 66, 79, 80; 600/109, 111; H04N 13/00, 15/00

(56) References Cited

U.S. PATENT DOCUMENTS

| | | | |
|---|---|---|---|
| 3,186,300 | 6/1965 | Littmann | 88/39 |
| 4,167,302 | 9/1979 | Karasawa | 350/36 |
| 4,253,447 | * 3/1981 | Moore et al. | 600/109 |
| 4,873,572 | * 10/1989 | Miyazaki et al. | 348/45 |
| 5,408,265 | 4/1995 | Sasaki | 348/70 |
| 5,557,154 | 9/1996 | Takahashi | 359/378 |
| 5,577,991 | 11/1996 | Akui et al. | 600/111 |
| 5,579,772 | 12/1996 | Kinukawa et al. | 128/665 |
| 5,646,680 | * 7/1997 | Yajima | 348/74 |
| 5,860,912 | 1/1999 | Chiba | 600/111 |

* cited by examiner

Primary Examiner—Howard Britton
Assistant Examiner—Nhon T Diep
(74) Attorney, Agent, or Firm—Pandiscio & Pandiscio

(57) ABSTRACT

A method and apparatus are provided for correcting for optical misalignment of the dual (left and right) images produced by a stereo electronic endoscope, or of the corresponding dual images produced by coupling electronic imaging devices to each of two monocular teaching ports of a stereo optical endoscope. The stereo image alignment technique comprises electronically capturing the video image data of the dual images, and subsequently processing that data electronically to correct for optical alignment errors. The method involves digitizing the electronic data and digitally performing the equivalent of vertical image shift, and/or image size change, and/or image rotation as required to correct for any visual image misalignment.

19 Claims, 11 Drawing Sheets

METHOD AND APPARATUS FOR ALIGNING STEREO IMAGES

FIELD OF THE INVENTION

This invention relates to a method and apparatus for aligning left and right images generated by an electronic stereo camera and more particularly to stereo endoscopes and operating microscopes.

BACKGROUND OF THE INVENTION

A three-dimensional ("3D") vision endoscope or microscope, hereinafter referred to as a "stereo" endoscope or microscope, comprises a stereoscopic optical system for forming a 3D image of an object. The stereoscopic optical system comprises objective lens means arranged to pick up two slightly different images of a object that approximate the two views (left and right) provided by human binocular vision. The difference between the two views is known as parallax. By properly aligning and presenting the two optical target images to human binocular vision, a three-dimensional sense of the target is presented to the viewer.

In the case of a conventional (non-electronic) optical endoscope or microscope the two optical target images picked up by the objective lens means are passed to a viewing system in the form of a binocular eyepiece unit comprising two like optical channels each having, inter alia, a focusing lens followed by an ocular lens. In the case of an electronic stereo endoscope or microscope, the images picked up by the objective lens means are passed to an electronic stereo camera. As used herein the term "electronic stereo camera" is intended to denote a camera comprising two solid state electronic imaging devices, typically charge coupled devices (CCD's), that are capable of generating electrical output signals representative of images received thereby. The camera may also include electronic circuit means for controlling operation of the imaging devices so as to produce said output signals. Alternatively, some or all of said electronic circuit means may be disposed outside of the camera. The camera may also comprise image formation optics for relaying images and focusing them on the imaging devices. Also as used herein the term "video camera head" is intended to designate a camera having a single electronic imaging device, with or without associated electronic circuit means for controlling its operation so as to produce a useful output signal representative of the images received by said imaging device. Hence a stereo video camera essentially comprises two video cameras heads. The video camera head also may also comprise image formation optics for relaying images and focusing them on the imaging device.

The output signals of the electronic imaging devices are processed to provide video signals that in turn are used to drive an electronic viewing (display) system. The latter may comprise a conventional video monitor that is operated so as to provide a stereoscopic display in response to the video signals, the stereoscopic display typically being generated so as to be viewable by special polarized spectacles or, in the case where left and right images are displayed alternately, by spectacles having shutters that alternately block each eye in synchronism with alternate displaying of the left and right images. The viewing system also may be a head-mounted display unit, comprising first and second miniature electronic display devices, one for each eye, that display the left and right images respectively. The form of display system used is not critical to the invention.

The capability of the human brain to fuse two images to produce a three-dimensional visual effect is tolerant of misalignment errors between the two images. However, only a small degree of misalignment, in the form of differences in image size, vertical position and rotation, will cause viewer discomfort, and such discomfort increases as a function of the degree of misalignment. Consequently prolonged viewing of misaligned stereo images, such as occurs in cardiac surgery or pneurosurgery operations, can produce a high degree of viewer discomfort.

In the optical domain, it is possible to align images by physically moving lenses, prisms, CCD's and other optical devices. However, in the case of a stereo endoscope the size limitation on the insertion portion of the endoscope results in the optical elements being quite small, making it difficult to mechanically adjust components to correct for misalignment errors.

U.S. Pat. No. 5,577,991, issued Nov.26, 1996 to N. Akui et al, discloses various methods for adjusting left and right images to correct for mismatch. FIG. 3 of that patent discloses a method and apparatus for electronically correcting for optical mismatch errors, while other figures of that patent show mechanical means for optical systems of images. Mechanical methods and means for correcting for misalignment errors of the type described are expensive and are not fully satisfactory for a number of reasons. The electronic method embodied in the system of FIG. 3 of said patent is not explained or illustrated in specific detail but appears to have certain limitations. Nevertheless, it is recognized that the equivalent of horizontal and vertical image shift, image size change, and image rotation can be performed very effectively in the electronic domain.

OBJECTS AND SUMMARY OF THE INVENTION

Accordingly, the primary object of this invention is to provide a new and improved method and means for electronically correcting for misalignment of stereo images generated by solid state imaging devices in electronic video cameras, especially where such cameras form part of or are coupled to stereo endoscopes and operating microscopes.

Another object is to provide a method and apparatus for correcting for stereo images misalignment that differs from and improves upon the electronic system shown in FIG. 3 of said U.S. Pat. No. 5,577,991.

A further object is to provide a new and improved stereo image alignment technique for endoscopes and operating microscopes which involves capturing electronically generated left and right images which may contain residual optical alignment errors and subsequently processing those images electronically to correct those errors.

Still another object is to provide a method and apparatus for correcting stereo image misalignment problems which involves automatically capturing left and right electronic images (video image data), digitizing those images, processing the digitized images to achieve alignment, and processing the aligned digitized images to generate signals for driving a stereo display device.

These and other objects are achieved by passing left and right channel video signals derived from first and second CCD's to analog-to-digital (A/D) signal converters to generate digitized video image data, inputting the digitized images to a stereo image processor that comprises first and second frame memory units for storing the video image data, and an image analysis computer for comparing the digitized images inputted to said first and second frame memory units, using said computer to compare the digitized left and right images inputted to said first and second frame memory units and to determine the sense and degree of mismatch between said digitized left and right images, generating correction command signals according to the sense and degree of mismatch between said digitized left and right images, inputting those command signals to said frame memory units as readout control signals to control the readout of video image data from said frame memory units, passing the digitized data read out from said memory units to digital to analog converters so as to generate analog video signals, and passing said analog video signals to a stereo display device. By way of example, the preferred embodiment of the invention may be used in conjunction with a head-mounted binocular electronic display, but the stereo display device may also be a TV-type monitor. Also preferably in the case of an endoscope, the video signals are derived from a video camera that comprises an integral part of an electronic stereo endoscope. An alternative embodiment involves a stereo-optical operating microscope having two auxiliary observation ports, one for each optical channel, which are commonly identified as "teaching ports". A monocular electronic video camera head is coupled to each observation port, with the left and right video image signals derived from the two monocular camera heads being used drive a display after being processed to correct stereo misalignment errors.

THE DRAWINGS

FIGS. 4–7 illustrate the concept of digital electronic image processing and particularly the concept of separating data entry and data readout addressing sequences so as to effect corrections of various forms of misalignment;

Figure 1:
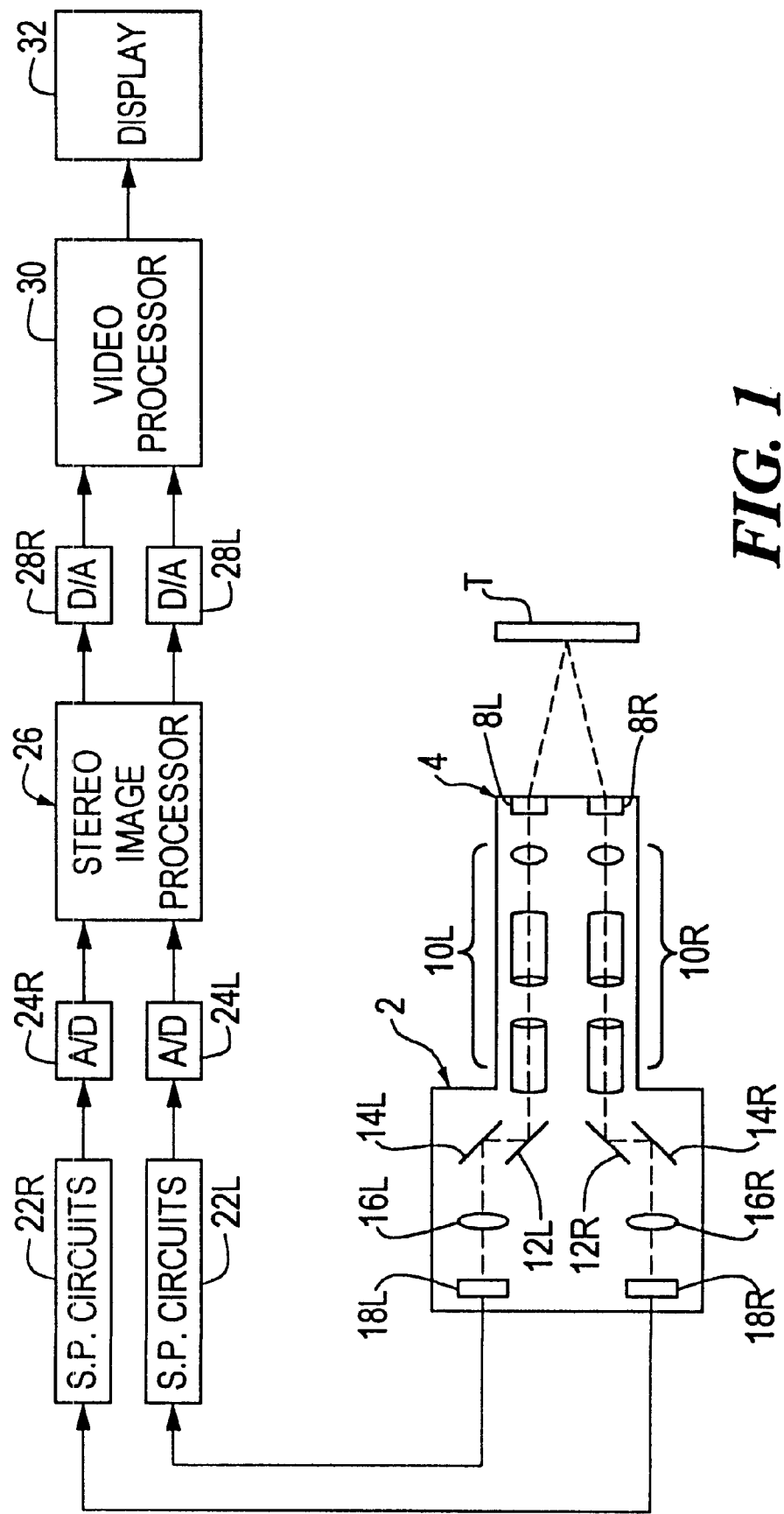
FIG. 1 is a diagrammatic illustration of the general arrangement of an endoscope system and an image alignment measuring and adjusting system embodying the present invention.
Figure 2:
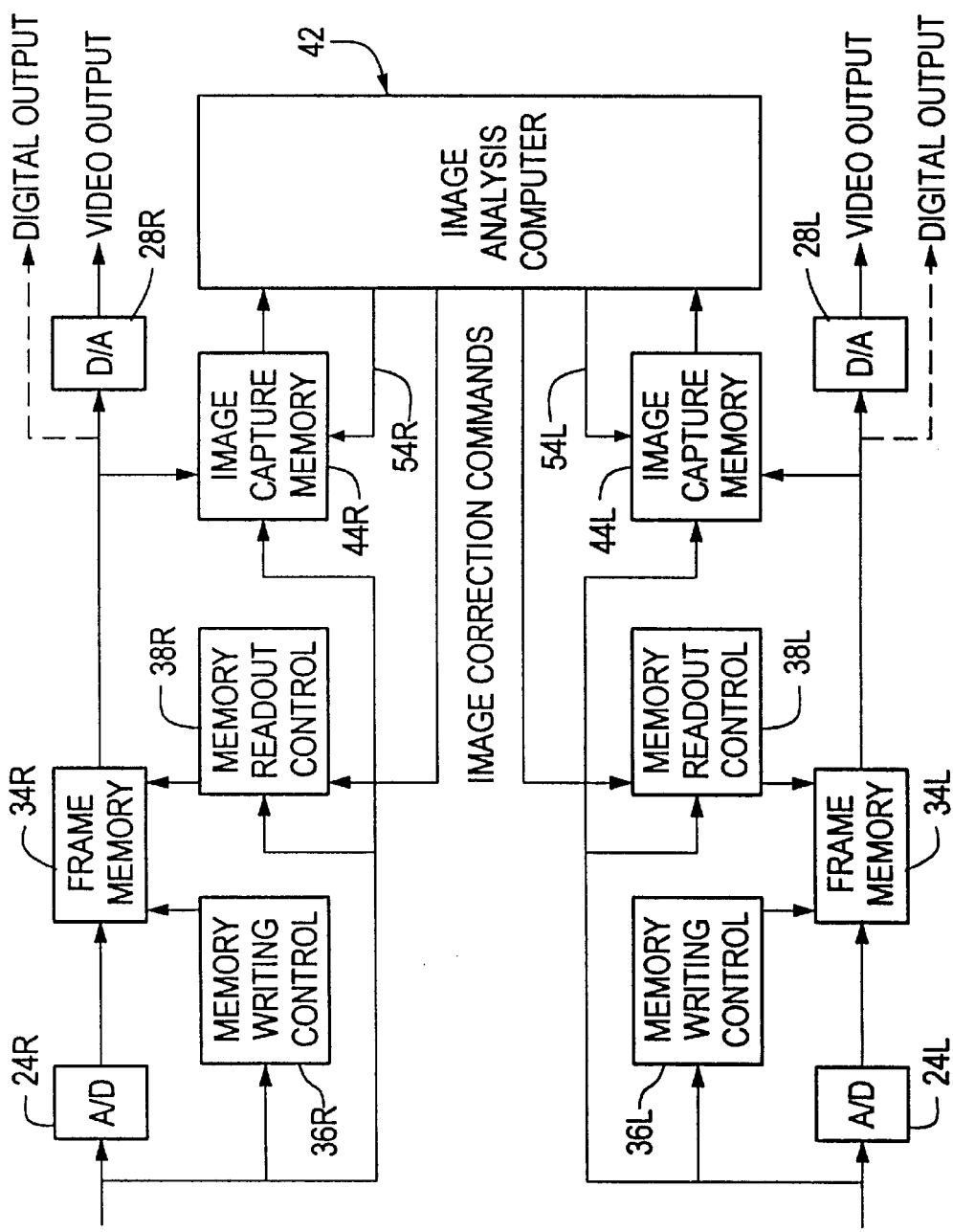
FIG. 2 is a diagrammatic illustration similar to FIG. 1 but providing details of the image alignment measuring and adjusting system.
Figure 3:
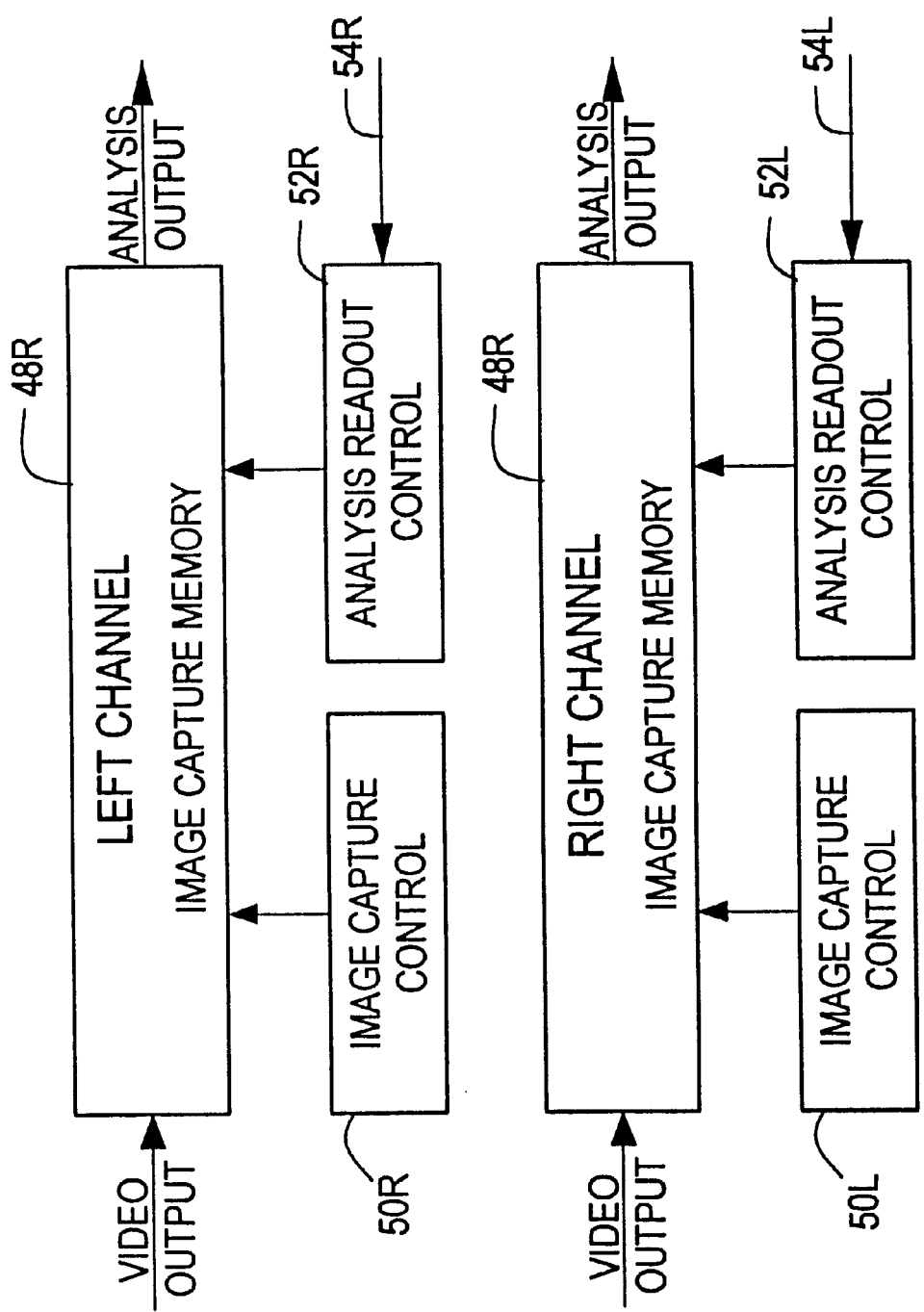
FIG. 3 illustrates certain details of the image capture memory shown in FIG. 2.
Figure 9A:
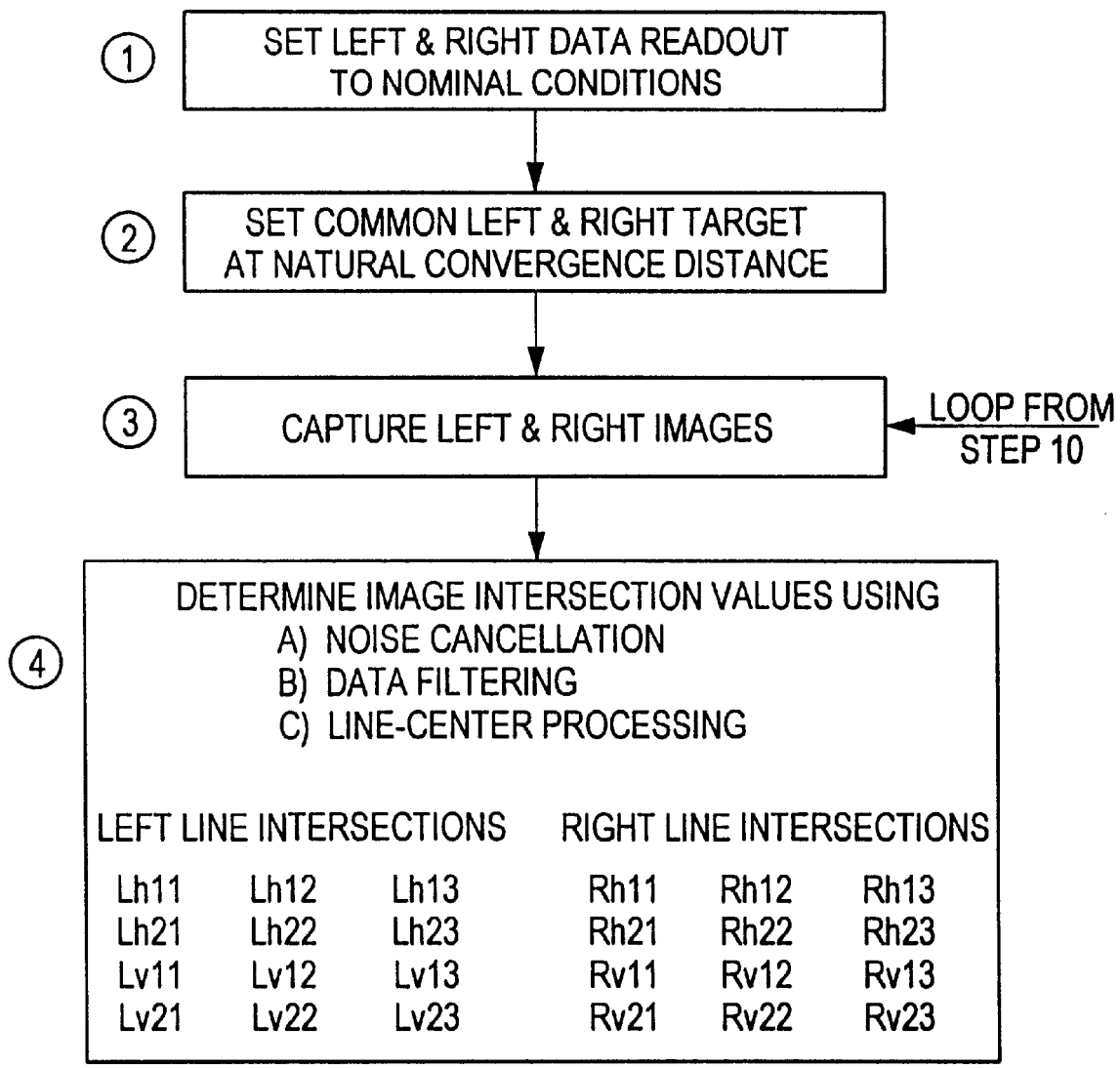
Figure 9B:
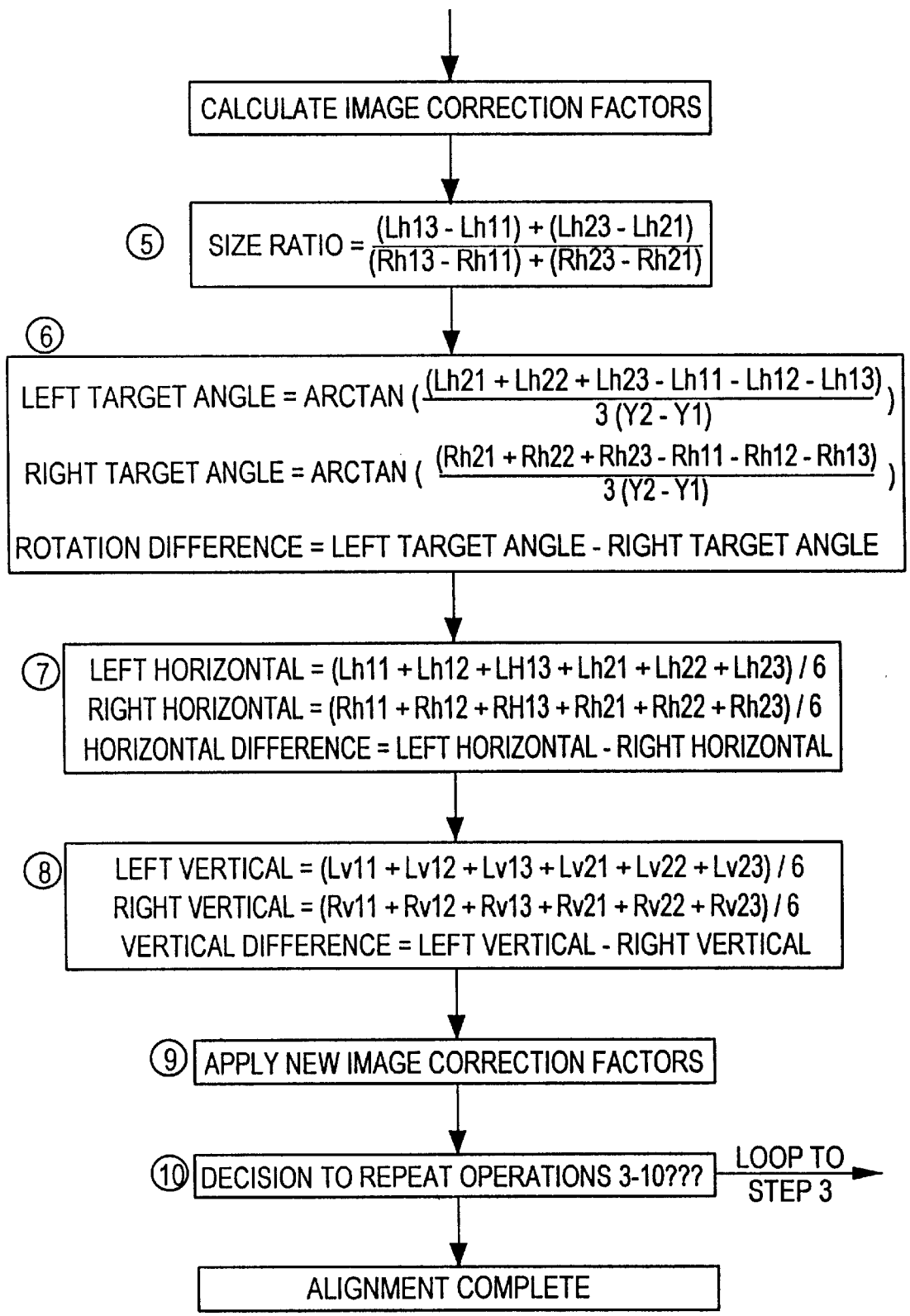
Figure 10:
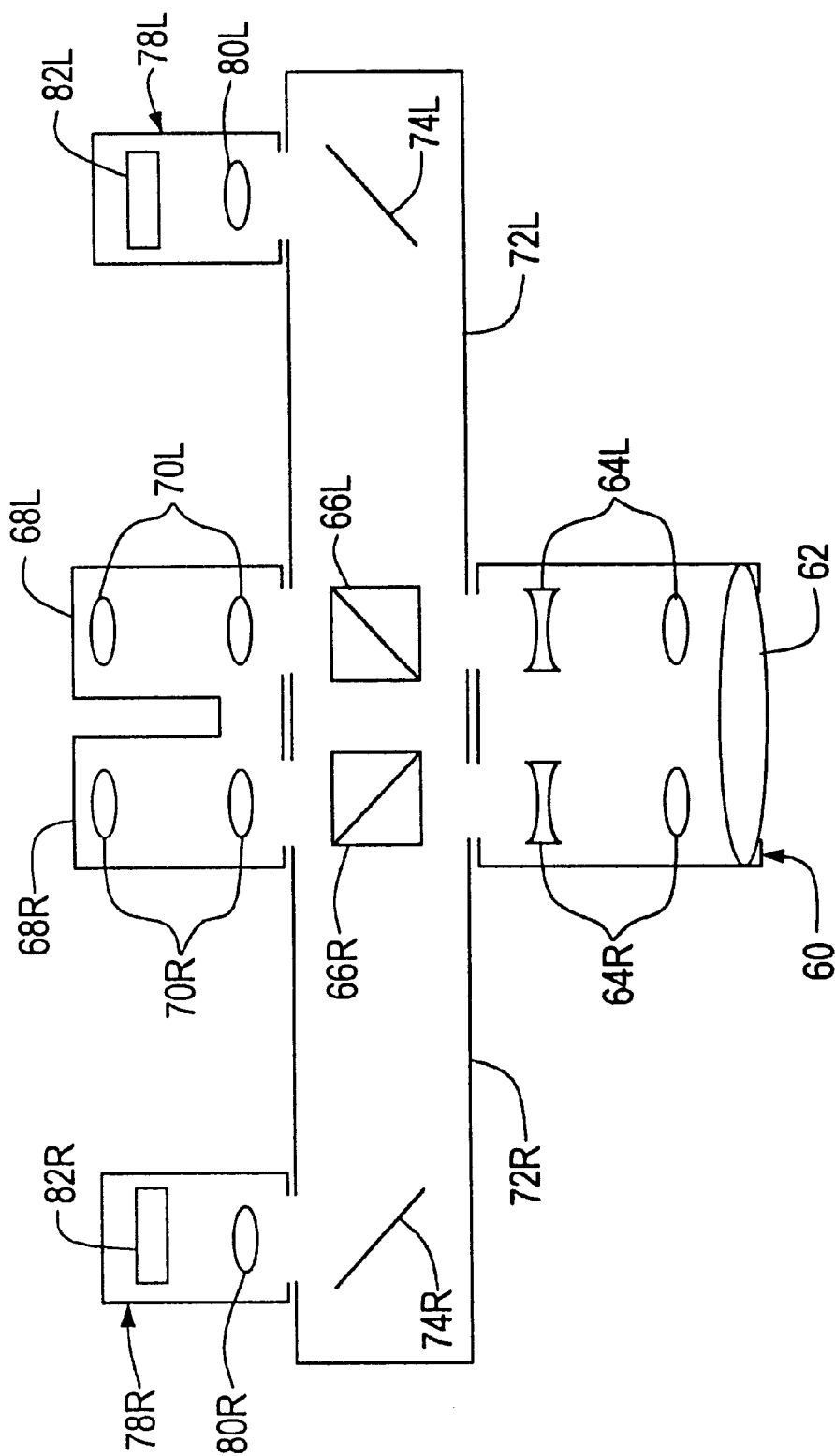

FIGS. 9A and 9B constitute a computer software flow diagram indicating one form of computer program required to correct misalignment problems using the system shown in FIGS. 1–3;

FIG. 10 illustrates a stereo operating microscope having video camera heads coupled to each of its two teaching ports, the image alignment measuring and adjusting system of FIG. 2 making it possible to align the images formed by the two video camera heads to provide an electronically generated stereo display based on the right and left images transmitted by the microscope's two optical systems to the two cameras.

In the several figures, like components or elements are designated by like numerals.

DETAILED DESCRIPTION OF INVENTION

FIG. 1 illustrates diagrammatically a preferred form of image alignment measuring and adjusting system embodying the invention in combination with an electronic stereo endoscope. The latter comprises a housing 2 having a tubular insertion portion or barrel 4 containing two objective lenses 8R and 8L and two sets of relay lenses 10R, 10L. The housing also contains two pairs of 45° mirrors 12R, 12L and 14R, 14L, and a pair of focusing lenses 16R, 16L. The foregoing optical components form two observation optical systems or channels, one right ("R") and the other left ("L"). The endoscope also contains a stereo video camera comprising two electronic imaging devices 18R and 18L, e.g., two CCD's, positioned to pick up left and right images with parallax between them that are focused by lenses 16R, 16L. Alternatively and preferably, each imaging device may be an RBG imaging device (not shown) that comprises a color resolution prism, an R-imaging CCD, a G-imaging CCD, and a B imaging CCD (see FIGS. 11 and 31 of U.S. Pat. No. 5,579,772 for illustrations of RBG imaging devices coupled to a color-resolving prism.

Figure 7:
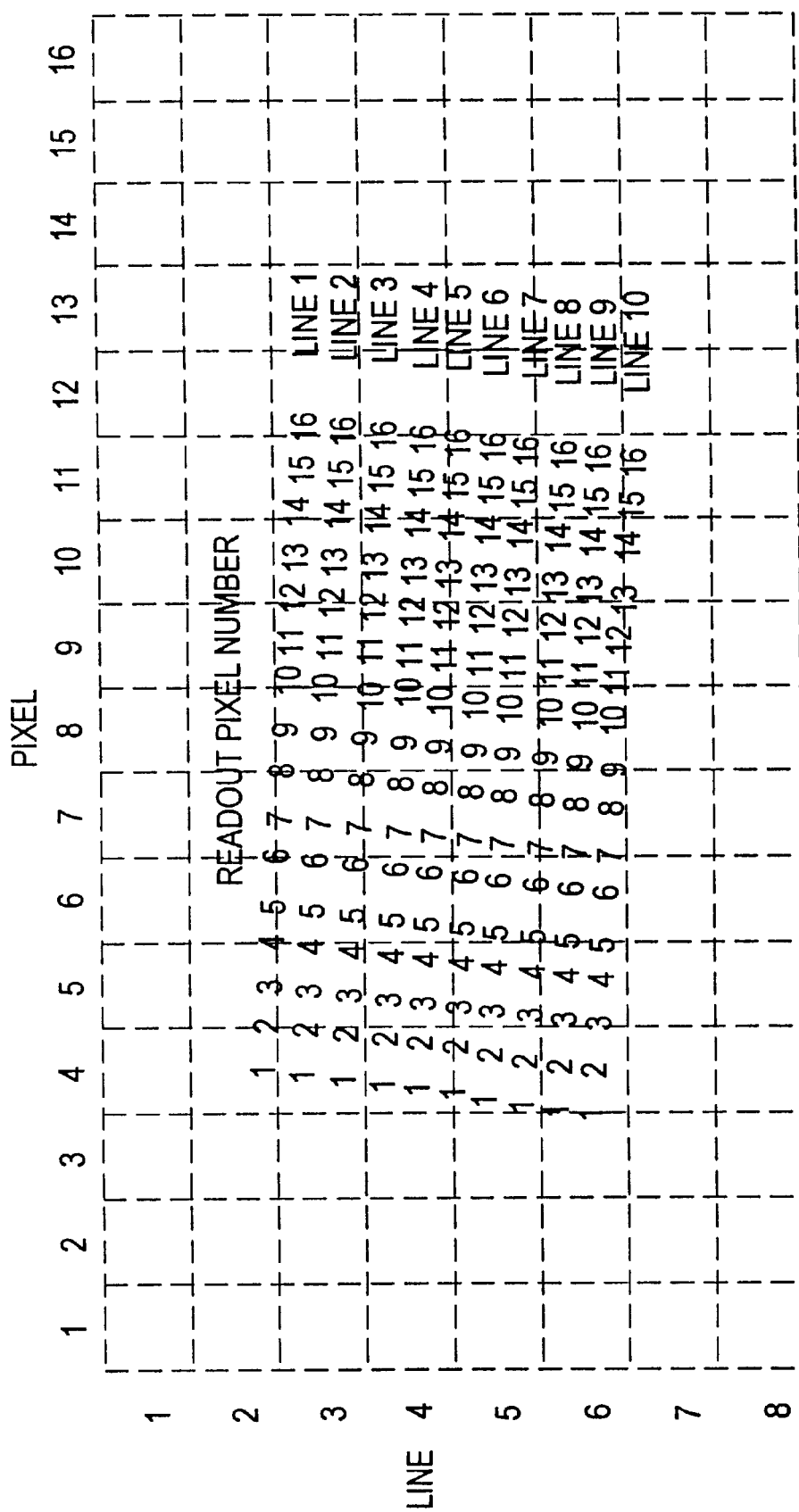
Figure 8:
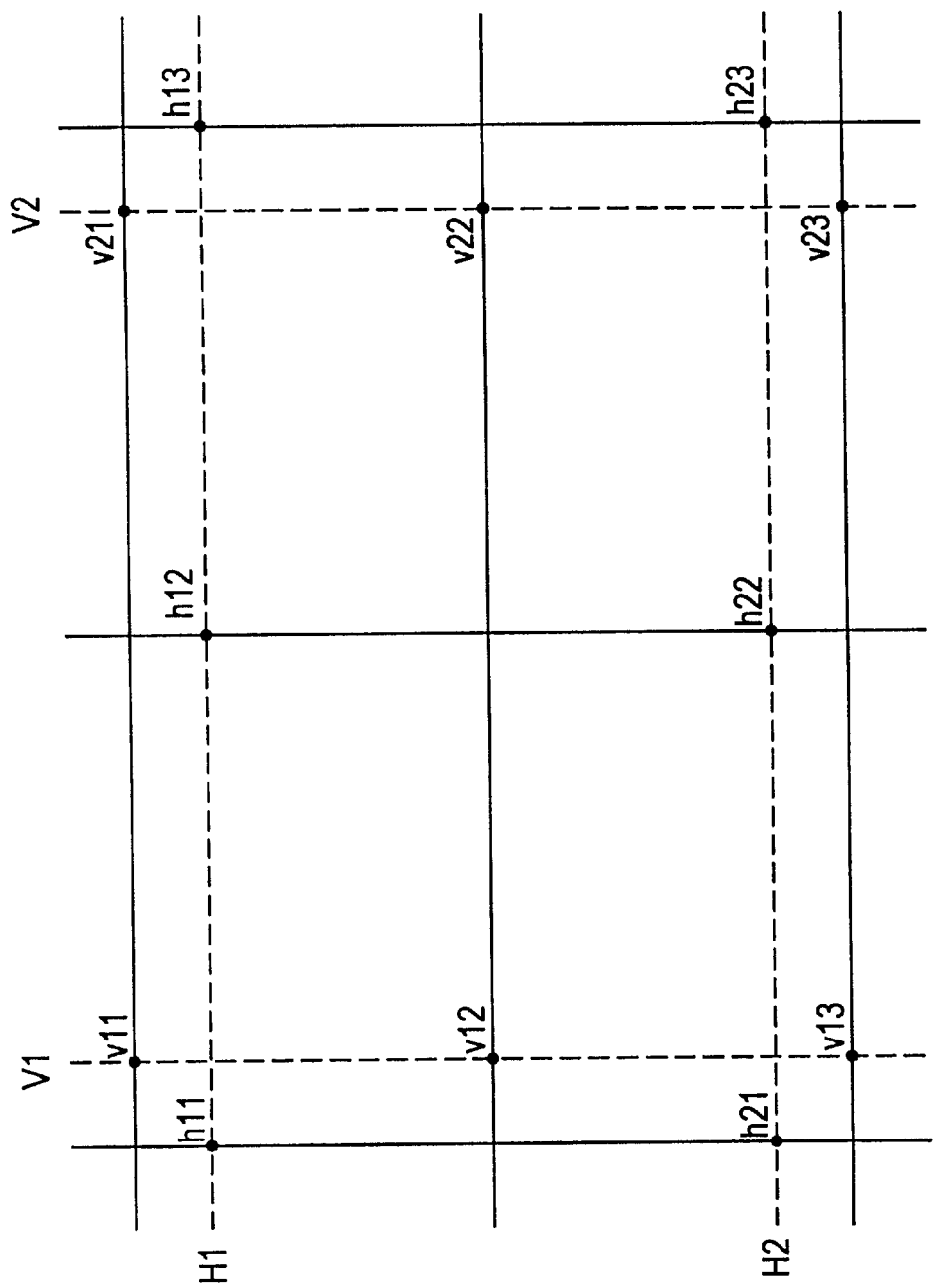
FIG. 8 illustrates a target used in measuring and correcting for image misalignment.

Although the camera is shown as built into housing 2 as an integral part of the endoscope, it is to be understood that the camera may be constructed as an independent stereo unit, or as two independent monocular video cameras, that are permanently or releasably attached to the endoscope, in the manner illustrated in FIGS. 7 and 8 of U.S. Pat. No. 5,577,991. The significant thing is that the endoscope comprises two optical channels or image formation systems and two imaging devices 18R and 18L. The output terminals of the imaging devices are connected to control and signal processing circuits 22R and 22L. The latter drive the CCD units and process the electrical signal outputs from those units so as to generate video signals. In passing through units 22R and 22L the output signals from the CCD's are amplified and linearized and then analog video output signals representing sequential frames of the images seen by the CCD's are produced from those amplified and linearized signals. Such control and signal processing units are well known to persons skilled in the video art. In the case of RGB imaging devices, the control and signal processing circuits 22R and 22L amplify and process the individual R, G and B output signals and generate therefrom an RGB video signal. The video signal outputs from the control and signal processing circuits 22R and 22L are then passed to analog-to-digital (AD) converters 24R and 24L where they are digitized. The digital output from converters 24R and 24L are then applied to a stereo image processor module 26 designed according to this invention which looks for and measures misalignment errors between the R and L images represented by the digitized video signals, and then corrects for any discerned misalignment errors. The digital signal outputs of image processor module 26 representing the corrected digitized video images are then passed to digital-to-analog converters 28R and 28L, and the analog video signal outputs from those converters are fed to a video processor unit 30 which comprises circuits for processing and formatting the R and L video signals for use in driving a stereo video display unit 32. The circuits required for video processor 30 are well known to persons skilled in the video art, as exemplified by U.S. Pat. No. 4,253,447 issued to W. C. Moore et al for "Color Endoscope With Charge Coupled Device And Television Viewing".

FIG. 2 presents further details of the preferred form of the image processor module 26. Although the A/D converters 24R and 24L and the D/A converters 28R and 28L are shown as discrete components separate from module 26, it is to be appreciated that they may be embodied in and form part of the image processor module itself. The latter comprises two dual-port image frame memory units 34R and 34L, with memory writing control circuits (i.e., writing address sequence generators) 36R and 36L coupled to one port and memory readout control circuits (i.e., readout address sequence generators) 38R and 38L coupled to the second port. Dual port memory units offer the advantage that data can be read out from one location while simultaneously new data is entered into any other location. The memory writing control circuits 36R and 36L control the entry of data from the A/D converters 24R and 24L and cause memory units 34R and 34L respectively to receive (read) such data on a frame-by-frame basis. The memory readout control circuits 38R and 38L cause data representing each image frame to be read out of the two memory units 34R and 34L respectively on a frame by frame basis in accordance with image correction instructions received from an image analysis computer 42. The digitized image data read out from memory units 34R and 34L are fed to the D/A converters 28R and 28L respectively. Additionally the same image data is fed to image capture memory units 44R and 44L, which in turn read that data out to computer 42 as hereinafter described. It is to be noted that control and signal processing circuits 22R and 22L produce control signals which are applied to memory writing control circuits 36R and 36L, memory readout control circuits 38R and 38L, and image capture memory units 44R and 44L, whereby those circuits are clocked in synchronism with each image frame represented by the video signal outputs from signal processing circuits 22R and 22L respectively. This control and clocking arrangement is represented in FIG. 2 by lines connecting the input line to A/D converters 24R and 24L to memory control circuits 36R and 36L, memory readout control circuits 38R and 38L, and image capture memories 44A and 44L.

FIG. 3 illustrates details of image capture memory units 44R and 44L. These units comprise random access memories 48R and 48L, image capture control circuits 50R and 50L (i.e., writing address sequence generators) and analysis readout control circuits 52R and 52L (i.e., readout address sequence generators). The input lines for memories 48R and 48L labeled "video output" are connected to the output lines of dual-port image frame memory units 34R and 34L respectively. The clocking of image capture memories mentioned above is achieved by applying the control signals produced by signal processing circuits 22R and 22L to image capture control circuits 50R and 50L and analysis readout control circuits 52R and 52L. Readout of image data from memories 48R and 48L into computer 42 is controlled by readout commands provided by image analysis computer 42 via lines 54R and 54L (FIGS. 2 and 3).

The invention is based on the concept that stereo images misalignment in electronic endoscopes and microscopes involves one or more of the following: (1) vertical shift, i.e., one image is slightly above or below the other, (2) one image is rotated relative to the other, and (3) one image is too large or too small relative to the other. These errors can be corrected by separately storing the two digitized images in memory, then reading out all or only a portion of the data representing each image in a selected order calculated to properly align the two images, and then by storing the appropriate alignment compensation values into the stereo image processor's memory readout controls 38R and 38L.

FIGS. 4–7 illustrate the concept of digital electronic image processing, and particularly the concept of separating data entry and date readout addressing sequences. These figures illustrate a section of an image stored in memory unit 34L or 34R that is 8 lines by 16 pixels. The squares represent memory locations while the line and pixel numbers represent both data entry addressing sequences and date readout (in bold numerals) addressing sequences. The illustrations could equally well apply to video data storage "by the frame" or "by the field".

Figure 4:
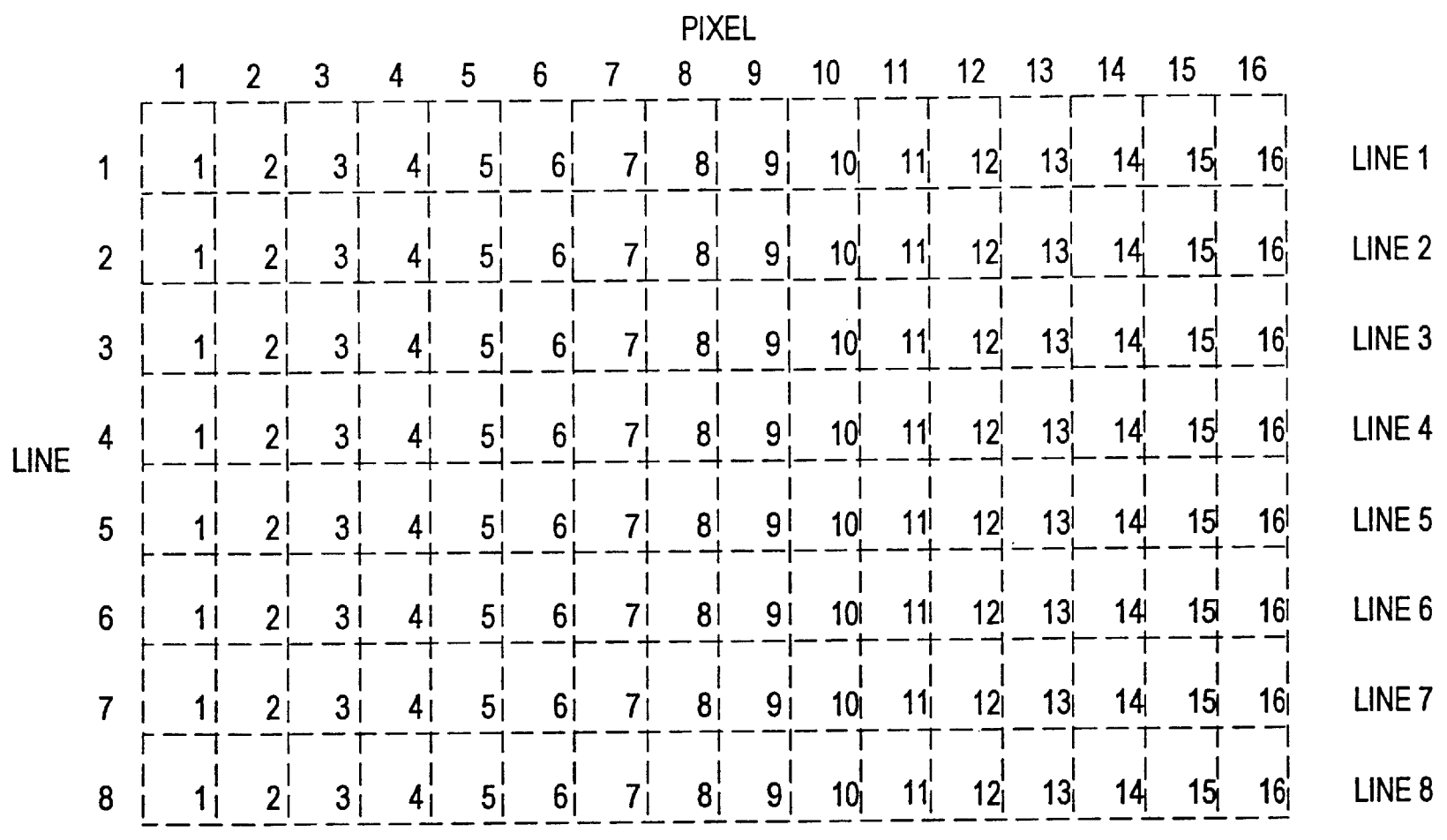

FIG. 4 illustrates data being read in and read out with identical addressing sequences. Hence data entered from input line 1 is read out as output line 1, with identical alignment of pixel positions on each line. Consequently a readout from memory of the image data stored in memory unit 34R or 34L as illustrated in FIG. 4 produces an output exactly identical to the input data, and, therefore, the video data output from the memory unit exactly equals the video input to that memory.

Figure 5:
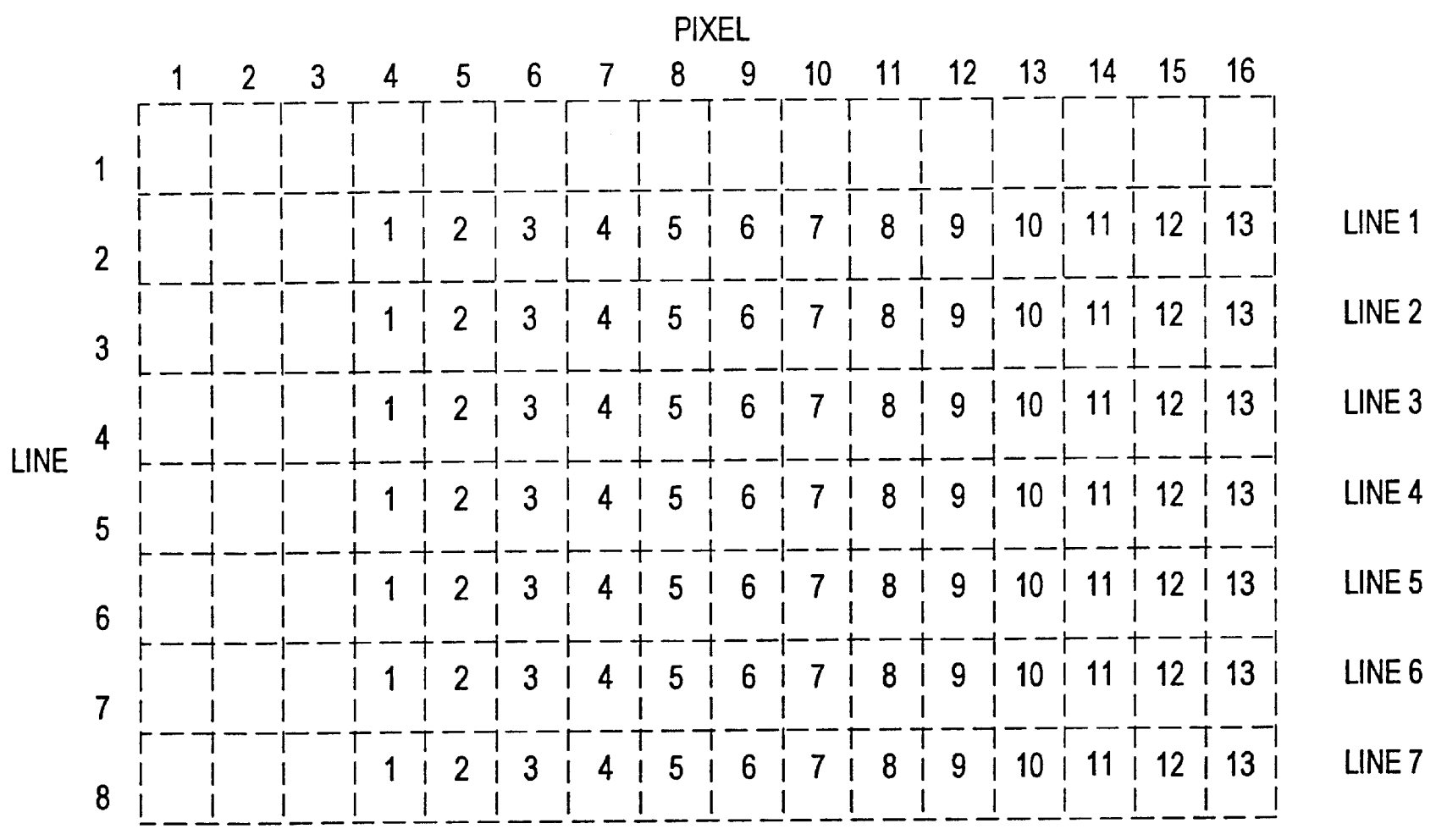

FIG. 5 illustrates data entry and data readout with slightly different addressing sequences. In this case assume that digitized image data was read into the memory unit exactly as shown in FIG. 4. However, data is read out in a different sequence. More specifically, data entered from input line 1 is not read out at all, and the same is true of the first 3 pixels from all subsequent lines. Thus the read out of data from memory produces an output that is not equal to the data input. Essentially the output video data is shifted vertically up 1 line and horizontally left 3 pixels. This capability to move the output image signal generated by one imaging device in a way different from the output image signal of another imaging device is the fundamental basis of the image alignment technique of this invention.

Figure 6:
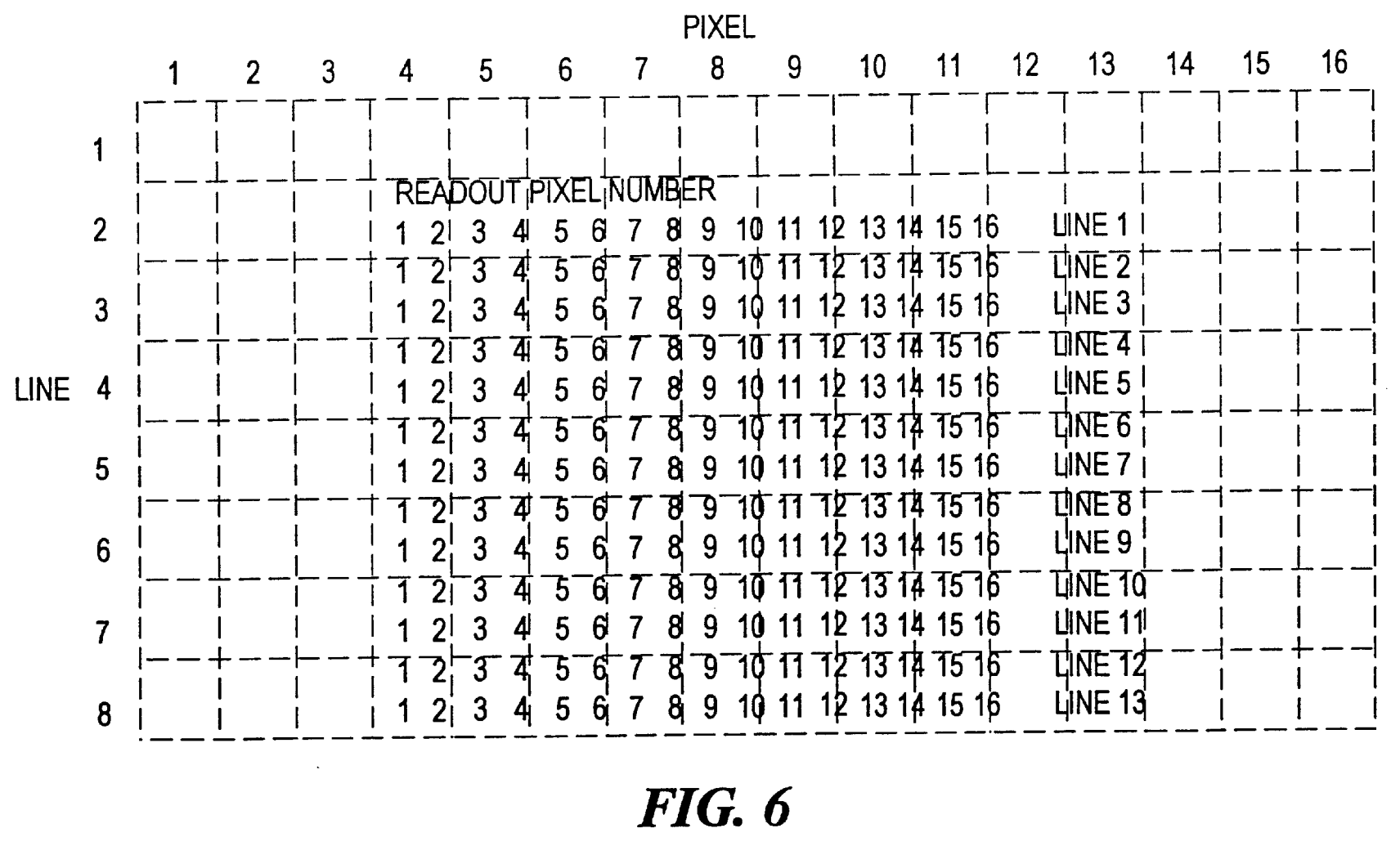

FIG. 6 illustrates another mode of addressing the memory units. In this case data is entered into and read out of a memory unit with radically different addressing sequences in order to achieve a magnification of a portion of a video image. Again assume that digitized image data was read into the memory unit exactly as shown in FIG. 4. However readout begins with pixel 4 of line 2. The second data readout is again pixel 4 of line 2. The same double readout occurs vertically, as output lines 2 and 3 both are read from data captured from input line 3. Thus the output video produced is generated from only a portion of the input image captured. In fact the output video generated with these addressing sequences is a linear 2:1 (4:1 area) magnification.

The simple repetition of successive pixels and successive lines would create a magnified blotchy representation of the original input image. However, this blotchiness can be reduced substantially by a process called interpolation. In such process, output data values are generated by considering not only which pixels and which lines are being read out for any given output pixel, but also the values of other pixel data nearby. In particular each output address can be viewed as an integer part and a fractional part in both vertical and horizontal directions. The integer parts can be used to select which input pixel data points shall participate in a mathematical function to generate the output data, while the fractional parts can be used to weight the contribution of the various selected input pixels.

FIG. 7 illustrates rotation as well as magnification of image data. In this case, data is read out so that it performs a linear 2:1 (4:1 area) magnification of the input data, but also a rotation of the output video image relative to the input video image. It should be noted also that as an output line is traversed, the input line required for providing its data shifts in midline. This arbitrary sequence shift from input to output is the reason that the readout addressing mechanism must permit random access.

In the practice of this invention, it is preferred that misalignment errors be corrected by changing only the R or the L video image according to the foregoing technique, while processing the other image unchanged. However, the system may be programmed so that in the event of relatively large misalignment errors, the correction be effected by changing each of the two video images by one-half of the total amount of change required to achieve correct alignment.

FIG. 8 and the following description explain how stereo-pair misalignment can be measured and corrected by this invention. FIG. 8 illustrates a calibration target used to measure misalignment, the target comprising a grid of horizontal and vertical lines. The image analysis computer 42 is programmed so as to carry out the following procedure for measuring and correcting for stereo-pair misalignment using the target of FIG. 8. The procedure is as follows:
1. The endoscope is mounted so that it is pointed at the target shown in FIG. 8, with the target located at the natural convergence distance for the R and L optical observation channels of the endoscope, as represented in FIG. 1 by target T. This is the distance at which the two images should be the most alike. In fact if there are no alignment errors, they will be identical.
2. The computer 42 sets the input and output channel address sequence generators 36R, 36L, 38R, and 38L for both the left and right channels to identical nominal conditions, with the result that the digitized video output of both memory units will be as illustrated in FIG. 4.
3. The computer 42 causes memory units 34R and 34L to capture R and L images of the entire target, or preferably an appropriate subset of both images consisting of the four lines H1, H2, V1 & V2 using a subsystem such as illustrated in FIG. 8. In this subsystem, the data corresponding to light intensity along lines H1, H2, V1 & V2 are available, and it is possible to associate the position of analysis output data points with image pixel position and line position.
4. The computer determines the exact values of the intersections listed in FIG. 8, namely: Lh11, Lh12, Lh13, Lh21, Lh22, Lh23, Lv11, Lv12, Lv13, Lv21, Lv22, and Lv23 for the Left image, and Rh11, Rh12, Rh13, Rh21, Rh22, Rh23, Rv11, Rv12, Rv13, Rv21, Rv22, and Rv23 for the right image. Since the target has been positioned such that the two images are supposed to be identical, the differences between left and right intersection values are used to determine misalignment between left and right images. If desired for maximum accuracy, the computer may be programmed to apply various techniques for noise cancellation, data filtering and line center calculations. With such techniques sub-pixel accuracies are possible.
5. The computer calculates image size ratio as follows:

$$SIZE\_RATIO = \frac{(Lh13 - Lh11) + (LH23 - Lh21)}{(Rh13 - Rh11) + (Rh23 - Rh21)}$$

The result of this calculation is applied to adjust one or both of the dual-port memory data readout sequence generators 38R and 38L, so that subsequent use of the two dual-port memories will result in equal size images of the same target.
6. The computer calculates image rotation of each target image as follows:

$$LEFT\_ANGLE = \arctan\left(\frac{(Lh21 + Lh22 + Lh23 - Lh11 - Lh12 - Lh13)}{3(Y2 - Y1)}\right)$$

$$RIGHT\_ANGLE = \arctan\left(\frac{(Rh21 + Rh22 + RH23 - Rh11 - Rh12 - Rh13)}{3(Y2 - Y1)}\right)$$

where Y2 and Y1 are the line numbers for lines H2 and H1 respectively. The difference between Left_Angle and Right_Angle is the rotation misalignment between left and right images. These factors are applied to adjust the dual-port memory readout sequence generators 38R and 38B so that the resultant images will have equal rotation angles.
7. Once size and rotation adjustments have been accomplished a second image capture is performed automatically. As a result of the size and rotation adjustments, this second image has zero size and angle misalignment. This second image is used to correct horizontal and vertical offsets. The computer calculates horizontal offset misalignment as follows:

LEFT_HORIZ=(Lh11+Lh12+Lh13+Lh21+Lh22+Lh23)/6

RIGHT_HORIZ=(Rh11+Rh12+Rh13+Rh21+Rh22+Rh23)/6

The amount of horizontal misalignment is (LEFT_HORIZ_RIGHT HORIZ). This factor is applied to the dual port memory readout sequence generators 38R and 38L to correct the horizontal error.
8. The computer then calculates vertical offset misalignment as follows:

LEFT_VERT=(Lv11+Lv12+Lv13+Lv21+Lv22+Lv23)/6

RIGHT_VERT=(Rv11+Rv12+Rv13+Rv21+Rv22+Rv23)/6

The amount of vertical misalignment is (LEFT_VERT−RIGHT_VERT). The compute applies this factor to the dual-port memory readout sequence generators 38R and 38L to correct the vertical error.

FIGS. 9A and 9B together constitute a flow diagram illustrating the program required to execute the foregoing alignment procedure. The flow diagram is self-explanatory to one skilled in the art of computer programming.

It is to be noted that the invention may be practiced other than as described above. For one thing, the two dual port memory units 34R and 34L are not required, although their use is preferred. Thus it is contemplated to replace dual port memory unit 34R with two conventional random access memory units connected in parallel, with one of the replacement memory units being used for writing in data at the same time that data is being read out of the other replacement memory unit. Of course, the other dual port memory unit 34L would be replaced by two like conventional random access memory units that are connected in parallel and also would write data in and read data out on an alternating basis relative to one another.

It is to be noted also that the invention may be used with an endoscope or microscope that utilizes two objectives, one for each channel, instead of the single objective shown in FIG. 1.

The invention also has application to stereo operating (surgical) microscopes of the type having auxiliary viewing ports commonly called "teaching ports". FIG. 10 illustrates diagrammatically an operating microscope having a barrel 60 containing an objective lens 62 and right and left imaging channels comprising focusing lenses 64R and 64L, two beam splitters 66R and 66L, and two eyepieces 68R and 68L comprising lens pairs 70R and 70L forming a binocular viewing system. Barrel 60 has two side ports fitted with side tubes 72R and 72L. Two 45° mirrors 74R and 74L are mounted in the two tubes as shown. Attached to tubes 72R and 72L and communicating with the two mirrors via apertures in the two tubes are video camera heads 78R and 78L comprising focusing lenses 80R and 80L and electronic imaging devices 82R and 82L each in the form of a single CCD or an RBG imaging unit as described above. Beam splitter 66R splits the image focused thereon by focusing lenses 64R, transmitting it to lens pair 70R and also to mirror 74R, while beam splitter 66L splits the image focused thereon by lenses 64L, transmitting the image to ocular lens pair 70L and also to mirror 74L. As a result the binocular viewing system comprising lens pairs 70R and 70L provides one surgeon with a stereo image presentation, while camera head 78R sees only the image carried by the right channel and camera head 78L sees only the image carried by the left channel. However, according to this invention, the output image signals derived from camera heads 78R and 78L are fed to an image alignment system as shown in FIGS. 1 and 2, with the signal outputs of imaging devices 82R and 82L being inputted to control and signal processing circuits 22R and 22L respectively. Since it is obviously difficult to assemble an operating microscope as shown in FIG. 10 so as to achieve correctly aligned stereo image pairs, applying the output of camera heads 78R and 78L to a system as shown in FIGS. 1 and 2 will correct for any misalignment and provide a second surgeon with a stereo presentation via electronic display 32.

It should be noted that the particular optical channels illustrated in FIGS. 1 and 10 are presented by way of example only, and may be replaced by other optical systems of like purpose.

Thus it is contemplated that the microscope of FIG. 10 could be modified by replacing objective lens 62 with two smaller objectives, one for each channel as is common practice and as is the case with the endoscope represented in FIG. 1. The invention also is not limited to systems using a particular type of display device. Thus the display device may be a head-mounted unit or a conventional video monitor. The invention also can be used with display devices that are adapted to display the left and right images alternately or concurrently, according to well known techniques for presenting 3-D pictures.

It should be noted that the invention is not limited to stereo electronic endoscopes and microscopes but can be used for aligning the stereo images of any stereo electronic camera. Although the stereo image alignment components shown in FIG. 2 can be united as a separate test instrument for use by instrument manufacturers in aligning stereo microscopes, endoscopes, and stereo video cameras per se, the invention also may be incorporated as a permanent part of the electronics system of a microscope or endoscope. In the case where the stereo camera is a permanent part of an instrument such as an endoscope, the stereo alignment system shown in FIGS. 1–3 need not be incorporated into the instrument's electronic system, but instead the corrections determined to be necessary by computer 42 may be permanently stored in a non-volatile memory that is integrated into the instrument or its associated electronics, with the electronics programmed so that each time the instrument is activated the data recorded in the non-volatile memory will be accessed automatically and used to adjust the stereo images as fed to the display system. Furthermore, as suggested by the two broken lines labeled "digital output" in FIG. 2, the image alignment system of this invention may be modified by using the corrected digital video image data output from memory units 34R and 34L to drive a digital video display according to recently developed digital video techniques.

The invention has numerous advantages. The electronic system for correcting misalignment errors utilizes conventional components and the software required to control operation of computer 42 and the other parts of stereo image processor 26 is straightforward and imposes no unreasonable or costly hardware requirements. Best of all, the alignment can be accomplished rapidly and accurately.

Other modifications and advantages will be obvious to persons skilled in the art.

What is claimed is:

1. A stereo endoscope or microscope comprising:

an objective optical system for viewing an object and forming and transmitting first and second images of said object having a parallax between said first and second images;

first and second imaging means coupled to said objective optical system for picking up said first and second images respectively and producing first and second output signals representative of said first and second images respectively;

signal processing means for converting said first and second output signals to first and second video signals respectively;

image-correcting means responsive to said first and second video signals for (a) comparing said first and second video signals to determine misalignment of said images relative to one another, and (b) modifying one or both of said video signals to correct for misalignment of said first and second images relative to one another; and an electronic display means responsive to the first and second video signal output of said image-correcting means for reproducing said first and second images and displaying said reproduced images either alternately or concurrently for viewing as a 3-D image.

2. The stereo endoscope or microscope according to claim 1 wherein said first and second video signals are analog video signals representative of said first and second images on a frame-by-frame basis, and further wherein said image-correcting means comprises:

means for converting said first and second analog video signals to first and second digital data on a frame by frame basis; first and second memory units for receiving and storing said first and second digital data; write control means for controlling the writing of said first and second digital data into said first and second memory units; readout control means for controlling the reading out of said first and second digital data from said first and second memory units; means coupled to said first and second memory units for driving said electronic display means in response to said first and second digital data read out from said memory units; image analysis means coupled to said first and second memory units for comparing said first and second digital data as read out from said memory units to measure any relative differences in the (a) sizes, and/or (b) horizontal and vertical positions, and/or (c) rotational positions of said first and second images and for producing at least one correctional signal according to said relative differences; and means for applying said at least one correctional signal to said readout control means as a readout command so as to adjust the readout of digital data from at least one of said first and second memory units in a manner that eliminates said differences in the images represented by subsequent first and second digital data fed to said first and second memory units.

3. The stereo endoscope or microscope according to claim 2 wherein each of said first and second memory units is a dual port memory unit having first and second ports, with data being read into said memory units via said first ports and data being read out of said memory units via said second ports.

4. A stereo endoscope or microscope apparatus comprising:

a pair of optical systems for transmitting an image of an object as first and second images having a parallax between said first and second images;

a pair of imaging means for picking up said first and second images as transmitted by said optical systems and producing first and second output signals representative of said first and second images respectively;

a display means for displaying said two images either alternately or concurrently for viewing as a 3-D image;

image-correcting means responsive to said first and second output signals for correcting for misalignment of said first and second images relative to one another so that said images coincide with one another as displayed by said display means, said image-correcting means comprising first and second signal processing channels for processing said first and second output signals and producing first and second analog video signals therefrom, means for converting said first and second analog video signals to first and second digital data on a frame by frame basis; first and second memory units coupled to said first and second signal processing channels for receiving and storing said first and second digital data; write control means for controlling the writing of said first and second digital data into said first and second memory units; readout control means for controlling the reading out of said first and second digital data from said memory units; means coupled to said first and second memory units for driving a stereo display device in response to said first and second digital data read out from said memory units; image analysis means coupled to said first and second memory units for comparing said first and second digital data as read out from said memory units to measure any relative differences in the sizes, and/or horizontal and vertical positions, and/or rotational positions of said first and second images and for producing first and second correctional signals according to said relative differences; and means for applying said first and second correctional signals to said readout control means as readout commands so as to adjust the readout of digital data from at least one of said first and second memory units in a manner that eliminates said differences in images represented by subsequent first and second digital data fed to said first and second memory units.

5. A stereo microscope comprising:

first and second optical channels for viewing an object and forming and transmitting first and second images of said object having a parallax between said first and second images;

viewing means coupled to said first and second optical channels for displaying said first and second images for viewing as a 3-D image;

first and second imaging means coupled to said first and second optical channels respectively for picking up said first and second images respectively and producing first and second output signals representative of said first and second images respectively;

means for converting said first and second output signals to first and second digital video signals respectively;

image-correcting means responsive to said first and second digital video signals for (a) comparing said digital video signals to determine any misalignment of said images relative to one another, and (b) modifying said first and second video signals to correct for misalignment of said first and second images relative to one another; and an electronic display means responsive to said modified first and second video signals for reproducing said first and second images and displaying said reproduced images either alternately or concurrently for viewing as a 3-D image.

6. A microscope according to claim 5 wherein said image-correcting means comprises first and second signal processing channels for processing said first and second output signals and producing first and second analog video signals therefrom, means for converting said first and second analog video signals to first and second digital data on a frame by frame basis; first and second memory units coupled to said first and second signal processing channels for receiving and storing said first and second digital data; write control means for controlling the writing of said first and second digital data into said first and second memory units; readout control means for controlling the reading out of said first and second digital data from said memory units; means coupled to said first and second memory units for driving said electrical display means in response to said first and second digital data read out from said memory units; image analysis means coupled to said first and second memory units for comparing said first digital data as read out from said first memory unit to said second digital data as read out from said second memory unit so as to measure any relative differences in the sizes, and/or horizontal and vertical positions, and/or rotational positions of said first and second images and for producing first and second correctional signals according to said relative differences; and means for applying said first and second correctional signals to said readout control means as readout commands so as to adjust the readout of digital data from at least one of said first and second memory units in a manner that eliminates said differences in images represented by subsequent first and second digital data fed to said first and second memory units, whereby said reproduced images coincide with one another and are presented for viewing by said display means as a 3-D image.

7. The microscope according to claim 6 wherein each of said first and second memory units has first and second ports, with data being read into said memory units via said first ports and data being read out of said memory units via said second ports.

8. An apparatus for correcting for misalignment of the separate left and right images of a stereo electronic camera having a first and second optical means for transmitting an image of an object as first and second images having a parallax between said first and second images, and first and second imaging means for picking up said first and second images as transmitted by said optical systems and producing first and second output signals representative of said first and second images respectively said apparatus comprising:

first and second signal processing channels comprising means for generating first and second analog video signals in response to said first and second output signals respectively, said first and second video signals being representative of said first and second images on a frame by frame basis;

an electronic display means;

display operating means responsive to said first and second video signals for causing said display means to reproduce said first and second images on a frame by frame basis and display said reproduced first and second images either alternately or concurrently for viewing as a 3-D image;

image-correcting means for correcting for misalignment of said first and second images relative to one another so that said reproduced first and second images appear coincident with one another as a 3-D image as displayed by said display means, said image-correcting means comprising first and second means for converting said first and second video signals to first and second digital data representative of said first and second images respectively on a frame by frame basis, first and second memory units for receiving and storing said first and second digital data; write control means for controlling the writing of said first and second digital data into said first and second memory units; readout control means for controlling the reading out of said first and second digital data from said memory units; image analysis means coupled to said first and second memory units for comparing said first and second digital data as read out from said memory units to measure any relative differences in the sizes, horizontal and vertical positions, and rotational positions of said first and second images and for producing first and second correctional signals according to said relative differences; and means for applying said first and second correctional signals to said readout control means as readout commands so as to adjust the readout of digital data from at least one of said first and second memory units in a manner that eliminates any of said differences in images represented by subsequent first and second digital data fed to said first and second memory units respectively.

9. A method of correcting for misalignment of the separate left and right images of a stereo electronic camera having a first and second optical means for transmitting an image of an object as first and second images having a parallax between them, and first and second imaging means for picking up said first and second images as transmitted by said optical systems and producing first and second output signals representative of said first and second images respectively, said method comprising the steps of:

processing said first and second output signals so as to produce first and second analog video signals therefrom on a frame by frame basis;

converting said first and second analog video signals to first and second digital data on a frame by frame basis;

writing said first and second digital data to first and second memory units on a frame by frame basis;

reading out said first and second digital data from said first and second memory units on a frame by frame basis;

analyzing and comparing said read first and second data on a frame by frame basis to measure any relative differences in the sizes, horizontal and vertical positions and rotational positions of said first and second images and producing in response to said read first and second data first and second correctional signals according to said relative differences;

applying said first and second correctional signals as readout commands to said first and second memory units respectively so that the readout of digital data from at least one of said first and second memory units representing subsequent successive frames of said first and second images is adjusted in a manner that eliminates said differences in said successive frames of said first and second images.

10. The method of claim 9 further including the step of generating a visual display of said first and second images on a frame by frame basis in response to said first and second digital data read out from said memory units.

11. The method of claim 10 wherein said first and second digital data read out from said memory units also is converted to third and fourth analog video signals respectively, and said visual display is generated in response to said third and fourth analog video signals.

12. The method of claim 9 wherein said stereo camera is part of an endoscope.

13. The method of claim 9 wherein said stereo camera is part of a stereo microscope.

14. The method of claim 9 wherein each of said first and second memory units has first and second ports, with data being read into said memory units via said first ports and data being read out of said memory units via said second ports.

15. Apparatus according to claim 6 wherein said modified first and second video signals constitute the said first and second digital data read out of said first and second memory units.

16. Apparatus according to claim 8 wherein each of said first and second memory units is a dual port memory unit having first and second ports, with data being read into said memory units via said first ports and data being read out of said memory units via said second ports.

17. An apparatus for correcting for misalignment of the separate left and right images of a stereo electronic camera having a first and second optical means for transmitting an image of an object as first and second images with a parallax between said first and second images, and first and second imaging means for picking up said first and second images as transmitted by said optical systems and producing first and second output signals representative of said first and second images respectively, said apparatus comprising:

first and second signal processing channels comprising means for generating first and second analog video signals in response to said first and second output signals respectively, said first and second video signals being representative of said first and second images on a frame by frame basis;

analog-to digital converter means for converting said first and second analog video signals into first and second digital data representative of said first and second images respectively on a frame by frame basis;

image-correcting means for correcting for misalignment of said first and second images relative to one another so that when said first and second images are reproduced by electronic display means they will appear coincident with one another for viewing as a 3-D image, said image-correcting means comprising first and second memory units for receiving and storing said first and second digital data, write control means for controlling the writing of said first and second digital data into said first and second memory units, readout control means for controlling the reading out of said first and second digital data from said memory units, image analysis means coupled to said first and second memory units for comparing said first and second digital data as read out from said memory units to measure any relative differences in at least the (a) sizes or (b) horizontal and vertical positions or (c) rotational positions of said first and second images and for producing first and second correctional signals according to said relative differences, and means for applying said first and second correctional signals to said readout control means as readout commands so as to adjust the readout of digital data from at least one of said first and second memory units in a manner that eliminates any of said differences in images represented by subsequent first and second digital data fed to said first and second memory units respectively;

digital-to-analog converter means;

means for applying said first and second digital data as read out of said first and second memories to said digital-to-analog converter means for producing first and second video output signals;

an electronic display means; and display operating means responsive to said first and second video output signals for causing said display means to reproduce said first and second images on a frame by frame basis and display said reproduced first and second images either alternately or concurrently for viewing as a 3-D image.

18. Apparatus according to claim 17 wherein each of said first and second memory units is a dual port memory unit having first and second ports, with data being read into said memory units via said first ports and data being read out of said memory units via said second ports.

19. A method of correcting for misalignment of the separate left and right images of a stereo electronic camera having a first and second optical means for viewing an object and transmitting first and second images of said object with a parallax between said first and second images, and first and second imaging means for picking up said first and second images as transmitted by said optical systems and producing first and second output signals representative of said first and second images respectively, said method comprising the steps set forth in FIGS. 9A and 9B of the drawings.

* * * * *